United States Patent [19]

Begin et al.

[11] 4,074,049

[45] Feb. 14, 1978

[54] ANTITHROMBOTIC 1,3,4-THIADIAZOLE

[75] Inventors: Louis E. Begin; Joseph E. Dunbar, both of Midland, Mich.

[73] Assignee: The Dow Chemical Company, Midland, Mich.

[21] Appl. No.: 743,200

[22] Filed: Nov. 19, 1976

[51] Int. Cl.$^2$ ............................................. C07D 413/4
[52] U.S. Cl. .................................... 544/82; 544/134; 260/243.3; 424/248.51; 260/306.8 D

[58] Field of Search .................... 260/246 B, 306.8 D

Primary Examiner—Nicholas S. Rizzo
Assistant Examiner—Jose Tovar
Attorney, Agent, or Firm—James W. Ambrosius

[57] ABSTRACT

A series of 1,3,4-thiadiazoles substituted in the 2,5-position with amino, dialkylaminoalkylthio, or heterocyclicalkylthio are useful as antithrombotic agents.

9 Claims, No Drawings

ANTITHROMBOTIC 1,3,4-THIADIAZOLE

BACKGROUND OF THE INVENTION

Adenosine diphosphate, hereafter called ADP, is a principal factor in the aggregation of blood platelets. Platelet aggregation in the blood stream of a mammal can lead to the formation of a thrombus. Agents which interfere with ADP-induced platelet aggregation are of use as antithrombotic drugs.

SUMMARY OF THE INVENTION

The compounds that are the subject of the present invention are represented by the general formula:

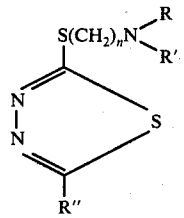

wherein $n$ is the integer 2, 3 or 4;

R and R' represent independent aliphatic hydrocarbon moieties of from 1 to 4 carbon atoms or taken together with the nitrogen atom represent a heterocyclic ring selected from the group consisting of pyrrolidinyl, azepinyl, and morpholinyl; and R" represents amino or a moiety having the formula

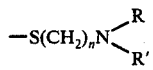

wherein $n$, R and R' are the same as defined above.

It is, therefore, understood that the compounds that are the subject of the present invention are 1,3,4-thiadiazoles with substitutions in the 2 and 5 position. At least one substitution is a dialkylaminoalkylthio or a heterocyclicalkylthio. The opposing substitution may either be the same as the first substitution or amino. These compounds have been shown to be effective as blood platelet aggregation inhibitors in mammals. Some of the compounds are also useful in agricultural applications for the control of tobacco black shank.

This invention also includes the pharmaceutically-acceptable salts of the 1,3,4-thiadiazole compounds described herein. As used in the specification and claims, the term "pharmaceutically-acceptable salts" refers to non-toxic acid addition salts of the thiadiazole compounds, the anions of which are relatively innocuous to animals at dosages consistent with good platelet aggregation inhibition so that the beneficial effects of the free base are not vitiated by side effects ascribable to the anions. Pharmaceutically-acceptable salts include those derived from mineral acids such as hydrochloric, hydrobromic, sulfuric and nitric acids and from organic acids such as acetic, lactic, maleic, succinic, fumaric, glutaric, citric, malic, p-toluenesulfonic; methanesulfonic, tartaric acids and the like.

One process suitable for preparing the compounds is by reacting a 2,5-dimercapto-1,3,4-thiadiazole alkali metal salt with a selected chloroalkylamine in an inert solvent to yield a compound having a general formula as described above substituted identically in both the 2 and 5 position. Alternately, compounds having one amino substitution are prepared from 5-amino-1,3,4-thiadiazole-2-thiol. The procedure described above may be summarized as follows:

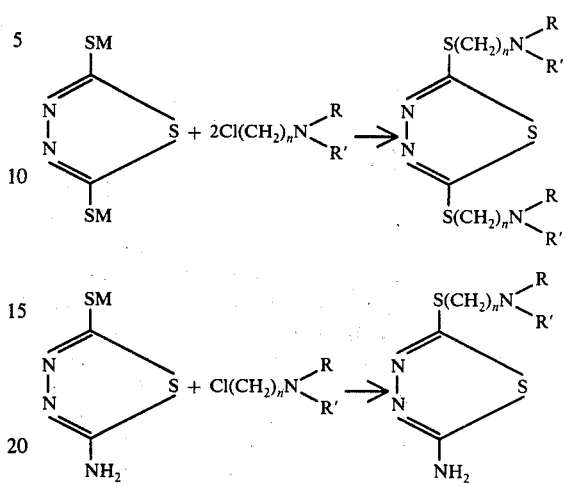

wherein $n$, R and R' represent the same moieties as defined above and M is an alkali metal.

Various inert solvents or mixtures thereof can be used in the preparation of the compounds of this invention. Suitable solvents include, for example, water, methanol, ethanol, propanol-2, n-propanol, dimethylformamide, dimethylsulfoxide, benzene, toluene and xylene. The solubility of the ingredients may vary from solvent to solvent and the exact solvent employed in a given preparation will depend upon the specific ingredients used to prepare the final product.

DETAILED DESCRIPTION OF THE INVENTION

It has been found that the 1,3,4-thiadiazole compounds when used in accordance with the invention and administered to mammals has the effect of inhibiting the ADP-induced aggregation of blood platelets. The compounds can be administered orally or parenterally by subcutaneous, intravenous or intraperitioneal injection or by implantation or the like, oral administration being preferred. The thiadiazoles are preferably administered as pharmaceutical compositions in dosage unit forms.

The following examples serve to further illustrate the invention, but are not to be construed as a limitation thereon.

EXAMPLE 1

Preparation of 2,5-bis(3-(4-morpholinyl)-propylthio)-1,3,4-thiadiazole

A mixture of 17.0 grams (0.075 mole) of 2,5-dimercapto-1,3,4-thiadiazole dipotassium salt and 24.5 grams (0.150 mole) of 4-(3-chloropropyl)-morpholine in 170 ml of water was heated under reflux with stirring for two hours. The mixture was then cooled to between 28 and 30° C and extracted with benzene. The benzene extract was washed with a saturated sodium chloride solution and dried over anhydrous sodium carbonate. After removal of the drying agent by filtration, the solution was evaporated to dryness, leaving the 2,5-bis(3-(4-morpholinyl)propylthio)-1,3,4-thiadiazole as a pale yellow oil. The product was recrystallized from methylcyclohexane to give white crystals with a melting point of 65.5°–66° C.

Elemental analysis showed carbon 47.6%, hydrogen 7.06%, and nitrogen 13.78% as compared to theoretical values of carbon 47.37%, hydrogen 7.21%, and nitrogen 13.81%.

EXAMPLE 2

Preparation of 2-amino-5-(2-(dimethylamino)ethylthio)-1,3,4-thiadiazole

A mixture containing 13.3 grams (0.100 mole) of 5-amino-1,3,4-thiadiazole-2-thiol, 17.2 grams (0.100 mole) of 2-chloroethyldiethylamine hydrochloride, 27.6 grams (0.200 mole) of potassium carbonate, 50 ml of dimethyl sulfoxide, and 50 ml of water was warmed to 75° C. Additional water was added to dissolve the salts. The mixture was stirred at 75° C for 20 minutes and cooled in an ice bath. The 2-amino-5-(2-(dimethylamino)ethylthio)-1,3,4-thiadiazole precipitated as a cream colored crystalline solid. The product was recrystallized from acetonitrile to give white crystals having a melting point of 140°-140.5° C.

Elemental analysis showed carbon 41.12 percent, hydrogen 6.98 percent, and nitrogen 24.01 percent as compared to theoretical values of carbon 41.35 percent, hydrogen 6.94 percent and nitrogen 24.11 percent.

EXAMPLE 3

Preparation of 2,5-bis(2-(diethylamino)ethylthio)-1,3,4-thiadiazole di-p-toluenesulfonic acid salt A mixture of 5.4 grams (0.025 mole) of 2,5-dimercapto-1,3,4-thiadiazole dipotassium salt, 8.6 grams (0.050 mole) of 2-chloroethyldiethylamine hydrochloride, 6.9 grams (0.050 mole) of potassium carbonate, 50 ml of dimethyl sulfoxide, and 50 ml of water was warmed to 65° C and stirred for 30 minutes. The mixture was cooled, diluted with water, and extracted with methylene chloride. The extract was dried over anhydrous magnesium sulfate, the solvent was removed by evaporation in vacuo, leaving the free base as an oil. The oil was dissolved in propanol-2, and the resulting solution was treated with a solution of a slight excess of p-toluenesulfonic acid in propanol-2 to give 2,5-bis(2-(diethylamino)-ethylthio)-1,3,4-thiadiazole di-p-toluenesulfonic acid salt as a white solid having a melting point of 123°-124° C.

Elemental analysis showed carbon 48.75 percent, hydrogen 6.49 percent, and nitrogen 8.16 percent as compared to theoretical values of carbon 48.53 percent, hydrogen 6.40 percent, and nitrogen 8.09 percent.

Other compounds falling within the scope of the present invention were also prepared using the general procedures already described. These compounds are as follows:
2,5-bis(2-(4-morpholinyl)ethyl-thio)-1,3,4-thiadiazole, m.p. 102.5°-103.5° C.
2,5-bis(2-dimethyl)ethylthio)-1,3,4-thiadiazole dihydrochloride, m.p. 228°-229° C.
2,5-bis(3-(dimethylamino)propylthio)-1,3,4-thiadiazole di-p-toluenesulfonic acid salt, m.p. 195°-196° C.
2,5-bis(2-(hexahydro-(1H)-azepinyl)ethylthio)-1,3,4-thiadiazole dihydrochloride salt, m.p. 236.5°-237.5° C.
2,5-bis(2-(1-pyrrolidinyl)ethylthio)-1,3,4-thiadiazole di-p-toluenesulfonic acid salt, m.p. 125°-127° C.

EXAMPLE 4

Emboli formed in the vascular system of mice in response to the administration of ADP cause a stroke-like response that prevents mice from staying on an inclined screen. To illustrate the platelet aggregation inhibition effect of the 1,3,4-thiadiazoles, ten mice were dosed by intraperitoneal injection with 60 mgs per kilogram of body weight of the compound 2,5-bis(2-(diethylamino)ethylthio)-1,3,4-thiadiazole di-p-toluenesulfonic acid salt (Example 3). One hour after compound administration, the mice were challenged with ADP (0.05 M mole/kg) by injection via the tail vein and placed on an inclined screen. Unprotected control mice not injected with thiadiazole were unable to maintain their position on the screen when given a similar injection of ADP.

Of the mice treated with 2,5-bis-(2-diethylamino)ethylthio)-1,3,4-thiadiazole di-p-toluenesulfonic acid salt, four (40%) of the mice were found to be protected from ADP challenge and were able to remain on the screen.

EXAMPLE 5

The effect of the thiadiazole compounds were also demonstrated by conventional techniques originally described by Born in Nature, 194, 927 (1962). Platelet aggregation was initiated in vitro by 0.125 to 0.25 mg/ml of ADP. Rat blood was collected into 3.0 percent trisodium citrate solution (1:10) by cardiac puncture undeer methoxyflurane anesthesia. The blood was centrifuged at 120 g for 10 minutes at room temperature and the supernatant platelet rich plasma was removed and diluted with lactated Ringer's solution containing the pyridazine aggregation inhibiting agent (1.0:1.5). Samples of 1.0 ml were pipetted into plastic test tubes and incubated for three minutes. Plastic equipment was used for all procedures. The concentration of the thiadiazole compound in micromoles inhibiting ADP aggregation by 50 percent ($IC_{50}$) was determined using changes in optical density as a indicium of platelet aggregation. From these data an activity curve can be prepared.

Using the above procedure the compound 5-bis(3-(4-morpholinyl)propylthio)-1,3,4-thiadiazole (Example 1) was compared to aspirin, a known antithrombotic agent. $IC_{50}$ $ADP_{max}$ is the amount of the test compound which inhibits maximum ADP-induced platelet aggregation by 50%. $IC_{50}$ $ADP_{slope}$ is the concentration of the test compound which inhibits the speed of the platelet aggregation by 50%. The results were as follows.

|  | $IC_{50}$ $ADP_{max}$ | $IC_{50}$ $ADP_{slope}$ |
| --- | --- | --- |
| Compound Example 1 | 6.28 μMoles | 9.41 μMoles |
| Aspirin | 12.8 μMoles | 18.1 μMoles |

The above data indicate that under the conditions of this test the compound of Example 1 was about twice as active as aspirin in the inhibition of ADP induced platelet aggregation.

EXAMPLE 6

Measurement of platelet aggregation in vivo was carried out using the technique described by Broersma, et al., Thomb. diath. Haemorrhag. 29, 201 (1973). Such determinations are based upon the measurement of the blood pressure proximal to a filter with 53 micron openings through which arterial blood flows. Platelet aggregation partially obstructs the filter with time causing a change in the pressure which is proportional to the degree of platelet aggregation (thrombosis).

Fasted male beagle dogs were anesthetized with sodium pentobarbital (35 mg/kg), heparinized (16.5 μ/kg, i.v.) and tested for platelet function using aggregometry. Compounds were administered intravenously in solutions having the pH adjusted to 7.4. The solution was infused at a rate of 15.3 ml/min to total volume of 5 ml/kg of body weight. Thrombus formation was observed using the filter occlusion technique outlined above. Platelet count, hematocrit, blood pressure, and heart rate were also measured.

Using the technique outlined above it was found that the compound 2,5-bis-(2-(4-morpholinyl)ethylthio)-1,3,4-thiadiazole reduced ADP induced platelet aggregation in the dog by 36 percent when administered at a dosage of 20 mg/kg after 4 hours.

As noted above the compound 2-amino-5-(2-(diethylamino)ethylthio)-1,3,4-thiadiazole (Example 2) was found to be effective in the control and killing of tobacco black shank when applied as a soil drench. When applied in a solution of 25 ppm the compound was found to give 100 percent control of the disease under the conditions of the test.

What is claimed is:

1. A compound of the formula

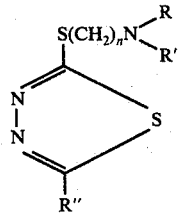

wherein $n$ is the integer 2, 3, or 4;

R and R' represent saturated aliphatic hydrocarbon moieties of from 1 to 4 carbon atoms or taken together with the nitrogen atom represent pyrrolidino, hexahydro-(1H)-azepinyl and morpholino;

and R" represents amino or a moiety having the formula

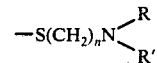

wherein $n$, R, and R' are the same as defined above or the pharmaceutically-acceptable non-toxic acid addition salts thereof.

2. The compound of claim 1 wherein R" is represented by the formula

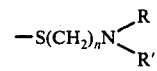

3. The compound of claim 1 which is 2-amino-5-(2-diethylamino)ethylthio)-1,3,4-thiadiazole or the pharmaceutically-acceptable non-toxic acid addition salts thereof.

4. The compound of claim 2 which is 2,5-bis(3-(4-morpholinyl)propylthio)-1,3,4-thiadiazole or the pharmaceutically-acceptable non-toxic acid addition salts thereof.

5. The compound of claim 2 which is 2,5-bis(2-diethylamino)ethylthio)-1,3,4-thiadiazole or the pharmaceutically-acceptable non-toxic acid addition salts thereof.

6. The compound of claim 2 which is 2,5-bis(2-(4-morpholinyl)ethylthio)-1,3,4-thiadiazole or the pharmaceutically-acceptable non-toxic acid addition salts thereof.

7. The compound of claim 2 which is 2,5-bis(2-(dimethylamino)ethylthio)-1,3,4-thiadiazole or the pharmaceutically-acceptable non-toxic acid addition salts thereof.

8. The compound of claim 2 which is 2,5-bis(2-(dimethylamino)propylthio)-1,3,4-thiadiazole or the pharmaceutically-acceptable non-toxic acid addition salts thereof.

9. The compound of claim 2 which is 2,5-bis(2-(hexahydro-(1H)-azepinyl)ethylthio)-1,3,4-thiadiazole or the pharmaceutically-acceptable non-toxic acid addition salts thereof.

* * * * *

UNITED STATES PATENT AND TRADEMARK OFFICE
CERTIFICATE OF CORRECTION

PATENT NO. : 4,074,049
DATED : February 14, 1978
INVENTOR(S) : Louis E. Begin and Joseph E. Dunbar It is certified that error appears in the above-identified patent and that said Letters Patent are hereby corrected as shown below:

Column 3, line 41 "sulfate, the" should read
-- sulfate, and the --;

Column 4, line 18 "(2-diethylamino)e-" should read
-- (2-(diethylamino)e- --;

Column 4, line 30 "undeer" should read -- under --;

Column 4, line 40 "a indicium" should read -- an indicium --;

Column 6, line 25 "2,5-bis(2-die-" should read
-- 2,5-bis(2-(die- --;

Signed and Sealed this

Tenth Day of October 1978

[SEAL]

Attest:

RUTH C. MASON
Attesting Officer

DONALD W. BANNER
Commissioner of Patents and Trademarks